United States Patent [19]

Koczab

[11] Patent Number: 4,826,498

[45] Date of Patent: May 2, 1989

[54] ABSORBENT PAD, PARTICULARLY FOR ARTICLES OF HYGIENE

[76] Inventor: Jean P. Koczab, 253 Domaine de la Vigne, F-59910 Bondues, France

[21] Appl. No.: 3,432

[22] Filed: Jan. 15, 1987

[30] Foreign Application Priority Data

Jan. 15, 1986 [FR] France ............................... 86 00522

[51] Int. Cl.$^4$ ............................................ A61F 13/16
[52] U.S. Cl. ................... 604/383; 604/367; 604/378; 604/384
[58] Field of Search ....................... 604/383, 367, 368; 28/103–107; 128/156; 428/234, 235

[56] References Cited

U.S. PATENT DOCUMENTS

| | | | |
|---|---|---|---|
| Re. 29,303 | 7/1977 | Fraser, Jr. et al. | 28/107 |
| 1,703,636 | 2/1929 | Rasch | 428/234 |
| 1,722,764 | 7/1929 | Rasch | 428/234 |
| 2,840,881 | 7/1958 | Bateman | 28/107 |
| 3,122,140 | 2/1964 | Crowe | 604/383 |
| 3,298,080 | 1/1967 | Smith | 428/234 |
| 3,811,445 | 5/1974 | Dostal | 604/383 |
| 4,102,340 | 7/1978 | Mesek et al. | |
| 4,250,172 | 2/1981 | Mutzenberg et al. | 428/234 |
| 4,357,386 | 11/1982 | Luciano et al. | 28/107 |
| 4,381,783 | 5/1983 | Elias | 604/368 |
| 4,539,982 | 9/1985 | Bailly | 128/156 |
| 4,685,914 | 8/1987 | Holtman | 604/367 |
| 4,718,899 | 1/1988 | Itoh et al. | 604/368 |

FOREIGN PATENT DOCUMENTS

0108637 5/1984 European Pat. Off. .

Primary Examiner—John D. Yasko
Assistant Examiner—Sharon Rose
Attorney, Agent, or Firm—Armstrong, Nikaido, Marmelstein & Kubovcik

[57] ABSTRACT

An absorbent pad, particularly for articles of hygiene such as diapers, nappy-pants, dressings, and the like, is disclosed which includes at least one sheet of long fibers, preferably one sheet of nonabsorbent fibers and the other of absorbent fibers, and superabsorbent particles distributed between the sheets. The superabsorbent particles are held in place by needling at least one of the long-fibered sheets.

11 Claims, 1 Drawing Sheet

ABSORBENT PAD, PARTICULARLY FOR ARTICLES OF HYGIENE

The present invention relates to an absorbent pad based on fibrous material, particularly for articles of hygiene such as diapers, nappy-pants, dressings and similar articles.

The absorbent pads used for various articles of hygiene such as diapers, nappy-pants, dressings for the incontinent, and the like, consists chiefly of fibrous absorbent materials, for example cellulose fibres. These fibrous materials are generally in the form of cellulose "fluff", that is to say very short cellulose fibres (length of the order of 1 to 2 mm) produced by dry grinding of paper pulp. The main disadvantage of these materials based on short fibres lies in the face that, in the wet state, they come apart, that is to say they loose their cohesion and they then agglomerate to form balls.

In order to improve the absorbency of such pads, it has already been proposed to incorporate therein particles of so-called superabsorbent material. Such superabsorbent materials generally consist of water-insoluble polymers capable of absorbing several times (at least fifteen times) their weight of liquid.

When the particles of superabsorbent material absorb liquid, they swell and they become a gelatinous mass. When close to each other, these gelatinous particles ten to agglomerate and can then form a layer which later prevents liquid passing through.

Very many proposals have been made in order to try and prevent this agglomeration of the swollen, gelatinous particles of the superabsorbent material, but in most cases they require additional operations (compression, embossing, heat treatment, and the like) on the sheet(s) acting as a substrate for the particles of superabsorbent material, and this leads to an increase in the cost of manufacture. Furthermore, the heat treatments generally result in a decrease in the absorbency of the particles of superabsorbent material, and hence a lower efficiency of the end product.

A subject of the present invention is an absorbent pad based on fibrous material, of simple structure, of reduced cost of manufacture, having good cohesion, not only in the dry state, but also in the wet state.

Another subject of the invention is an absorbent pad which ensures rapid diffusion of the liquid through the whole pad.

Furthermore, a subject of the invention is an absorbent pad capable of containing particles of superabsorbent material, in which the particles of superabsorbent material are satisfactorily held in position and run no risk of agglomerating in the swollen state.

The absorbent pad according to the invention, based on fibrous materials, particularly for articles of hygiene such as diapers, nappy-pants and dressings, comprises at least one sheet of fibres of a length which is at least equal to the thickness of the sheet, the sheet being bonded by needling or a similar process employing the fibres of the sheet to bond the latter.

It is by virtue of the use of long fibres instead of short fibres for forming the absorbent pad that it is possible to bond the latter by needling or a similar process and thus to endow the pad with good cohesion which the pad also retains in the wet state.

The absorbent pad may, for example, consist of a single needled sheet of fibres, but may advantageously comprise at least two sheets, each consisting of long fibres, the two sheets being bonded by needling or a similar process.

In this case, it may be advantageous to form at least one of the sheets, for example that which will be away from the body of the user of the article of hygiene, using absorbent fibres and to form another sheet, for example that which will be facing the user's body, using nonabsorbent fibres.

The particular advantage of an absorbent pad structure of this kind lies in the fact that absorbent fibres of at least one sheets are needled through the nonabsorbent sheet of fibres and thus form, through the latter, drainage promoting the flow of the liquid through the nonabsorbent sheet of fibres towards the sheet(s) of absorbent fibres.

According to a preferred embodiment, the absorbent pad additionally comprises particles of superabsorbent material between at least two sheets of long fibres bonded by needling or a similar process.

This not only makes it possible to considerably reduce the thickness of the absorbent pad for the same absorbency, but also by needling the sheets which between them receive the particles of superabsorbent material, to produce a trapping of the particles of superabsorbent material between the needling points, preventing, or at least reducing, the tendency of the particles of superabsorbent material to agglomerte in the swollen state.

Each of the long-fibre sheets of the pad according to the invention may be preneedled to itself before the combined sheets are needled together.

To improve the diffusion of the liquid through the whole pad, the pad according to the invention may also comprise a sheet of cellulose wadding between the sheets which are bonded by needling.

Furthermore, the pad according to the invention may be equipped with a sheet of nonwoven or cellulose wadding on at least one outer face of the pad, with a view to consolidating and improving the comfort of the pad.

A more detailed description will now be given, with reference to the attached diagrammatic drawings, of several embodiments illustrating, without implying any limitation, an absorbent pad according to the invention; in the drawings.

Figure 1:
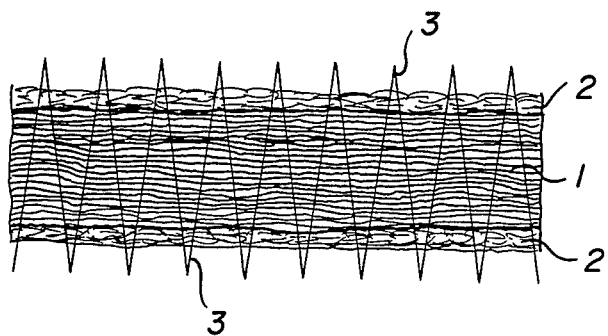
FIG. 1 is a partial diagrammatic section of an absorbent pad comprising a sheet of long absorbent fibres, which is lined with a layer of wadding on both sides.

According to FIG. 1, an absorbent pad consists of a sheet 1 of long absorbent fibres, with a length greater than the thickness of the sheet 1. The fibres of sheet 1 may be, for example, viscose fibres or alternatively acrylic fibres with a microporous structure such as the fibres marketed under the trademark "Dunova" by the Bayer company, F.R.G.

The fibre sheet 1 is lined on each face with a layer of cellulose wadding 2.

The sheet 1 lined with the layers of wadding 2 is needled from both sides, as shown diagrammatically by the lines 3, so that the needled fibres also pass through the two layers of wadding 2. This needling therefore ensures both a good cohesion of the fibre sheet 1 and the bonding of the wadding layers 2 to the fibre sheet 1.

Figure 2:
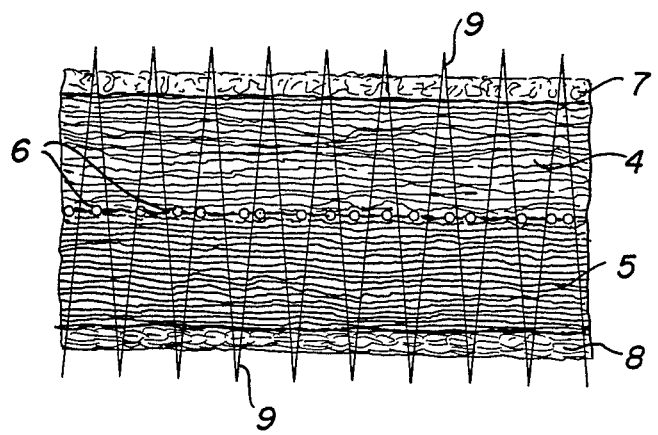
FIG. 2 is a partial diagrammatic section of an absorbent pad comprising two sheets of long fibres, one containing absorbent fibres and the other nonabsorbent fibres, which are lined externally, one with a layer of cellulose wadding and the other with a nonwoven, particles of superabsorbent material being arranged between the two sheets.

According to FIG. 2, an absorbent pad comprises two sheets 4, 5 of long fibres, it being possible for the sheet 4 to consist of nonabsorbent fibres, for example polyester fibres, and the sheet 5 of absorbent fibres, for example viscose fibres or acrylic fibres of microporous structure.

Between the two sheets 4, 5 there are arranged particles 6 of a commercial superabsorbent material, for example of polymers based on polyacrylic acid or of starch or cellulose derivatives produced by grafting, for example polysaccharide, alginate or carboxymethyl cellulose, in the form of powders, fibres, laminates, and the like. Such superabsorbent materials are marketed, for example, under the trademark "Aquakeep" by the Seitetsu Kagaku company, Japan.

The sheet 4 of nonabsorbent fibres is lined externally with a layer 7 of nonwoven, for example of viscose or of polyester, and the sheet 5 of absorbent fibres is lined externally with a layer 8 of cellulose wadding.

The two sheets 4, 5, the layer 7 of nonwoven and the layer 8 of cellulose wadding are bonded by needling the whole composite pad, from both sides, the fibres of the two sheets 4, 5 being needled so as to pass through the sheets 5, 4 and the layers 7, 8, respectively, as shown diagrammatically by the lines 9.

This needling of the sheets 4 and 5 by means of the long fibres not only provides each of the two sheets 4, 5 with good cohesion but also ensures the bonding of the sheets 4, 5 to the nonwoven layer 7 and to the wadding layer 8. Furthermore, this needling ensures the positioning of the particles of superabsorbent material 6, that is to say that the particles 6 are trapped between the needling points, so that there is not interference with their swelling, but that the swollen particles cannot agglomerate.

Lastly, the absorbent fibres of the sheet 5, needled through the nonabsorbent fibre sheet 4 and the nonwoven 7 form drainage which promotes the flow, through the nonwoven 7 and the nonabsorbent fibre sheet 4, of the liquid arriving onto the nonwoven 7, towards the sheets 5 which ensures the dispersion of the liquid over the whole pad, as well as the absorption of the liquid, together with the particles 6 of superabsorbent material.

From the point of view of manufacture, it may be preferable, if desired, to subject each sheet 4, 5 to a preneedling to the associated layer 7 or 8, and then to subject the two partial composite structures thus formed to a needling involving the whole composite pad formed in this manner.

It is obvious that the embodiments described above are given only by way of illustrative examples without implying any limitation and that many modifications and alternative forms are possible within the scope of the invention.

Thus, on a pad consisting of two sheets of long fibres, with particles of superabsorbent material between the two sheets, these two sheets could consists of absorbent fibres, identical or different, or of nonabsorbent fibres, identical or different, or of mixtures of absorbent fibres and nonabsorbent fibres.

It is also possible to incorporate in an absorbent pad according to the invention, comprising, for example, two sheets of long fibres, at least one thickness of short fibres, for example cellulose fibres (fluff), insofar as the needling of the whole pad using the fibres of the long-fibre sheets also makes it possible to simultaneously bond, and hence to consolidate, the layer of "fluff". This layer of "fluff" is then preferably situated between the two long-fibre layers, just as one or more sheets of cellulose wadding may be arranged between the two long-fibre sheets, especially to improve the diffusion of the liquid throughout the pad.

It has been found advantageous to use long fibres which, depending on the overall thickness of the pad, are between approximately 20 and 80 mm in length and between approximately 0.75 and 6 deniers in density.

The particles of superabsorbent material, in the form of grains, fibres or the like, may be employed preferably in a proportion of approximately 50 to 150 g/m$^2$ of pad.

Lastly, instead of performing a conventional needling, it would also be possible to use similar bonding processes employing the fibres of the sheets to be bonded, for example the process known by the name of "knit-stitching", employing no additional thread.

I claim:

1. A composite absorbent pad for diapers and sanitary napkins, comprising at least two superimposed layers of fibres and particles of super-absorbent material between said two layers, wherein a first of said at least two layers of fibres comprises of liquid-absorbent fibres having a length at least equal to the thickness of the second of said at least two layers, and the second of said two layers of fibres comprises of non-liquid-absorbent fibres, wherein said two layers or fibres being needled together with uniformly distributed needling points at least from the side of the said first layer of fibres remote from said second layer of fibres so that fibres of said first layer extend throughout said second layer of fibres, wherein the particles of super-absorbent material between said two layers of fibres being trapped between the needling points formed by said needled fibres, and wherein said uniformly distributed needled fibres of said first layer provide drains throughout said second layer of fibres for promoting the flow of liquid from the side of said second layer remote from said first layer throughout said second layer toward said first layer.

2. The pad according to claim 1, further comprising at least one sheet of cellulose wadding or cellulose fluff between said two layers of fibres, for improving the diffusion of liquid over the whole pad.

3. The pad according to claim 1, wherein said second layer of fibres consists of fibres of a length at least equal to the thickness of said first layer of fibres, a sheet of cellulose wadding is disposed on the side of said first layer of fibres remote from said second layer of fibres, and fibres of said first and of said second layers of fibres are needled from the side of said second layer remote from said first layer throughout said two layers of fibres and through said sheet cellulose wadding, thus bonding said sheet to said first layer of fibres by the said needled fibres.

4. The pad according to claim 1, further comprising a sheet of non-woven on the side of said second layer of fibres remote from said first layer of fibres, said needled fibres being also needled through said sheet so that said sheet is bonded to said second layer of fibres by said needling.

5. A composite absorbent pad for diapers and sanitary napkins, comprising at least two superimposed layers of fibres and particles of super-absorbent material between said two layers, wherein each of said at least two layers comprises of fibres having a length at least equal to the thickness of the respective layer and a first of said at least two layers of fibres comprises of liquid-absorbent fibres and the second of said at least two layers of fibres comprises of non-liquid-absorbent fibres, wherein said at least two layers of fibres being needled together with uniformly distributed needling points from the two opposite sides of the pad so that fibres of said first layer extend throughout said second layer of fibres and the fibres of said second layer extend throughout said first layer, wherein the particles of super-absorbent material between said two layers of fibres being trapped between the uniformly distributed needling points formed by said needled fibres, and wherein said needled fibres of said first layer provided drains throughout said second layer for promoting the flow of liquid from the side of said second layer remote from said first layer throughout said second layer toward said first layer.

6. The pad according to claim 5, further comprising at least one sheet of cellulose wadding or cellulose fluff between said two layers of fibres, for improving the diffusion of liquid over the whole pad.

7. The pad according to claim 5, wherein a sheet of cellulose wadding is disposed on the side of said first layer of fibres remote from said second layer of fibres, and fibres of said two layers of fibres are needled from the side of said second layer remote from said fist layer throughout said two layers of fibres and through said sheet of cellulose wadding, thus bonding said sheet to said first layer of fibres by said needled fibres.

8. The pad according to claim 6, further comprising a sheet of non-woven on the side of said second layer of fibres remote from said first layer of fibres, said needled fibres being also needled through said sheet so that said sheet is bonded to said second layer of fibres by said needling.

9. A composite absorbent pad for diapers and sanitary napkins, comprising at least two super-imposed layers of fibres; particles of super-absorbent material between said at least two layers; and at least one sheet of cellulose wadding or cellulose fluff between said at least two layers of fibres, wherein a first of said at least two layers of fibres comprises of liquid-absorbent fibres having a length of at least equal to the thickness of the second of said at least two layers and the second of said at least two layers of fibres comprises of non-liquid-absorbent fibres, wherein said two layers of fibres being needled together with uniformly distributed needling points at least from the side of said first layer of fibres remote from said second layer of fibres so that fibres of said first layer extend throughout said second layer of fibres, wherein the particles of super-absorbent material between said at least two layers of fibres being trapped between the uniformly distributed needling points formed by said needled fibres, and wherein said uniformly distributed needled fibres of said first layer provide drains throughout said second layer for promoting the flow of liquid from the side of said second layer remote from said first layer throughout said second layer toward said first layer and said at least one sheet of cellulose wadding of cellulose fluff.

10. The pad according to claim 9, wherein said second layer of fibres consists of fibres of a length at least equal to the thickness of said first layer of fibres, a sheet of cellulose wadding is disposed on the side of said first layer of fibres remote from said second layer of fibres, and fibres of said two layers of fibres are needled from the side of said second layer remote from said first layer throughout said first layer of fibres and through said sheet of cellulose wadding, thus bonding said sheet to said first layer of fibres by the said needled fibres.

11. The pad according to claim 9, further comprising a sheet of non-woven on the side of said second layer of fibres remote from said first layer of fibres, said needled fibres being also needled through said sheet so that said sheet is bonded to said second layer of fibres by said needling.

* * * * *